United States Patent
Gardner

(10) Patent No.: US 6,250,499 B1
(45) Date of Patent: Jun. 26, 2001

(54) TAM BOX

(76) Inventor: T. Marlene Gardner, 10401 Anderson Mill #106, Austin, TX (US) 78750

( * ) Notice: Subject to any disclaimer, the term of this patent is extended or adjusted under 35 U.S.C. 154(b) by 0 days.

(21) Appl. No.: 09/394,334

(22) Filed: Sep. 13, 1999

(51) Int. Cl.$^7$ .................................................. B23Q 7/04
(52) U.S. Cl. ............................................ 221/210; 221/260
(58) Field of Search .................................... 221/266, 241, 221/208, 210, 260, 191, 312 R, 277, 231, 259

(56) References Cited

U.S. PATENT DOCUMENTS

| | | | |
|---|---|---|---|
| D. 263,354 | 3/1982 | Jones | D6/86 |
| D. 309,067 | 7/1990 | Arrias | D6/515 |
| 3,445,037 | 5/1969 | Rothbaum | 221/196 |
| 4,057,172 | * 11/1977 | Olander | 221/260 |
| 4,308,974 | * 1/1982 | Jones | 221/196 |
| 4,530,200 | * 7/1985 | Prewer | 221/231 |
| 4,872,593 | * 10/1989 | Behringer | 221/231 |

* cited by examiner

Primary Examiner—Kenneth W. Noland
(74) Attorney, Agent, or Firm—Patent & Trademark Services; Thomas Zack; Joseph H. McGlynn

(57) ABSTRACT

A small portable apparatus to dispense various sized stored articles, such as tampons, from a container. The container's hollow interior mounts a rotatable flexible deformable roller which can both obstruct the movement of the contained articles against the force of gravity and, when rotated, permit their dispensing when engaged by the roller. Larger diameter articles cause more deformation of the roller's surface when compressed between the roller and the container's near adjacent side walls. Two external control knobs mounted on the same central shaft with the roller are used to manually rotate the roller into engagement with the articles.

2 Claims, 1 Drawing Sheet

TAM BOX

BACKGROUND OF THE INVENTION

Containers for the storage and dispensing of various shapes and sizes of contained articles are an everyday sight. Commercial containers of this type may be actuated by placing coins, bills or other money evaluate tokens into a slot or other opening which then permits a normally locked handle or button to be depressed to dispense the article. Such commercial dispensers are usually mechanically or electronically, or both, operated and complex. This adds to their price and limits their practical use to where their is sufficient cost and benefit justification available.

The present invention seeks to provide for a simple personal relatively inexpensive storage container which can dispense stored articles. As such it is simple to operate without the insertion of any coins or tokens and is operated by rotating an internal flexible roller which engages the stored articles to dispense them out of an opened lower front end exit opening. An upper closable lid on the container permits the insertion of additional articles to be dispensed. Particularly envisioned for dispensing are articles shaped to engage the roller such as tampons.

DESCRIPTION OF THE PRIOR ART

Gravity fed article dispensers for personal products such as tampons, cotton swabs, matches, etc. are well known. With such dispensers it is essential that their containers permit the storage of as many articles as possible and yet permit their individual dispensing one-article-at-time (e.g ... , see design patent Des. 309,067 to Arrias). Thus, the container's particular configuration and the mechanism to dispense the article is related to the articles to be dispensed in size and shape.

For example, in U.S. Pat. No. 3,445,037 to Rothbaum, the engaging mechanism of the dispenser is a rotatable mechanism while the articles dispensed, in this case elongated objects like toothpicks, matches or swabs, which engage the mechanism are stored and sized to permit their removal or dispensing one at a time from a container opening. The article obstructing and feeding mechanism in the Rothbaum invention is described as a rotatable roller that has a groove in its side journal led in the housing. This roller manually operated by an external housing knob to pick up the articles one at a time in the roller's groove to carry and drop them into a trough from which they may picked up by a user. Thus, the obstructing and carrying mechanism for the articles to be dispensed, the roller and its side groove, are related to the placement of the articles within the container, and their size and configuration.

In U.S. Pat. No. 4,308,974 to Jones the tampon dispenser for different sized tampons has an external housing handle and internal guiding shelves and dispensing pockets activated by the handle. Different sized tampons are said to be dispensed in the Jones patent.

The Jones design patent Des 263,354 shows a similar looking dispenser. In contrast to the obstructing and article engaging rollers of these inventions, the roller of the present invention is made of a flexible material such that it can accommodate itself to different shapes and sizes of articles to be dispensed as more further set forth in this specification.

SUMMARY OF THE INVENTION

This invention relates to an article dispensing container having a flexible deformable article engaging roller which can both obstruct the movement of the article within the container and be deformed to permit its dispensing by gravity.

It is the primary object of the present invention to provide for an improved gravity fed article dispensing apparatus.

Another object is to provide for such an apparatus specifically designed to dispense tampons of different sizes.

These and other objects and advantages of the present invention will become apparent to readers from a consideration of the ensuing description and the accompanying drawings.

DESCRIPTION OF THE PREFERRED EMBODIMENT

Figure 1:
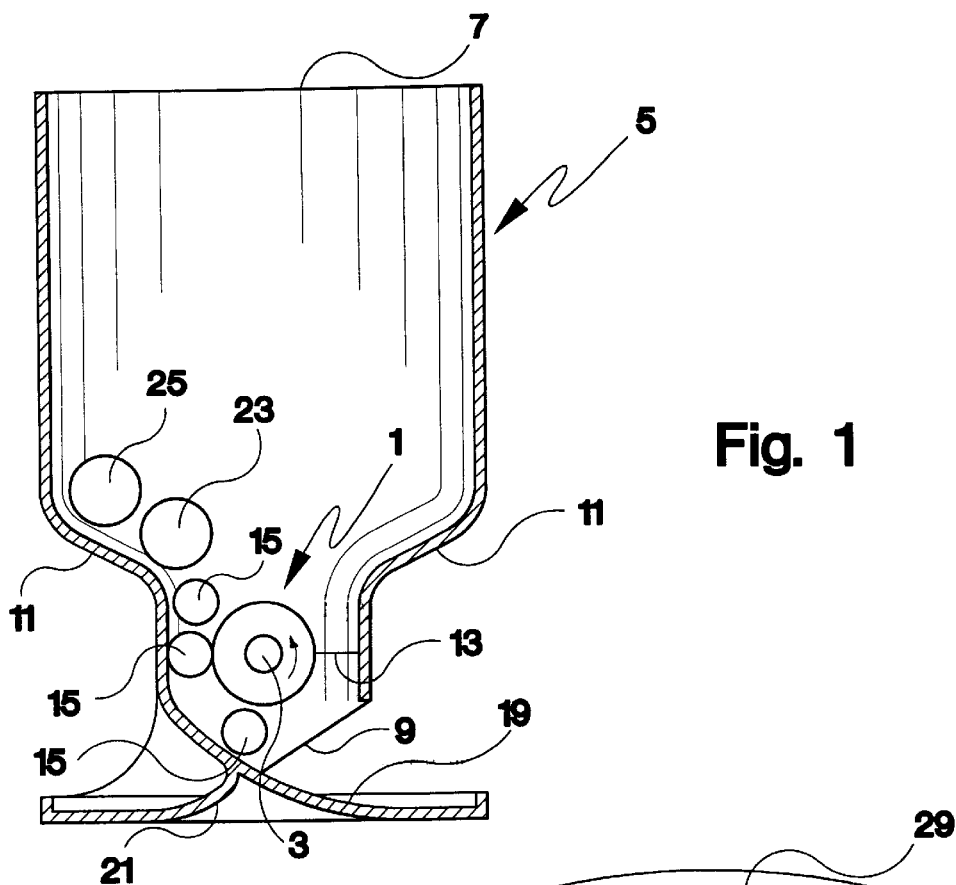
FIG. 1 is a side cross sectional view of the invention's preferred embodiment.

FIG. 1 is a side vertical cross sectional view of the invention's preferred embodiment with the near side exterior housing wall removed. Within the housing the interior flexible deformable cylindrical roller 1 is shown mounted on a central supporting shaft 3. The roller is shown from an end view. The roller's two opposite ends are journal on its central shaft into the housing's 5 two opposite side walls. The roller is made of a resilient deformable material than can retain its original shape after being subjected to compressive forces.

The hollow inverted bottle shaped housing 5 is closed on all sides except for its opened circular (when viewed from above) top 7 and its lower article dispensing exit opening 9. The housing's upper portion is generally uniform in cross section diameter until it reaches the lower tapered in sides 11. At the housing wall sides opposite roller 1, the shortest article passageway distance 13 between the roller's outer surface and the nearest housing wall, is shown in its undeformed state. Normally the distance 13 is slightly less than the cross section diameter of the smallest sized tampon or article to be dispensed.

The cross section diameter of tampon 15 shown represents this smallest article. When roller 1 is rotated into engagement with the article, shown in a counterclockwise direction, there is a slight surface deformation of the tampon and a more pronounced inward deformation of the flexible engaging roller surface as shown by the dotted lines 17. This roller deformation is caused by the compressive force of the tampon as it bears against the rotating roller and the adjacent housing surface wall. This roller deformation permits tampons of different cross section sizes to pass to the dispenser outlet.

For example, the smallest cross section diameter sized dispensed tampon (size 15) can pass by the roller through passageway 13 under the influence of gravity to the lower discharge opening 9. At this lower location a user removes the tampon from its holding tray portion 19. To permit the housing to stand upright, a second leg 21 shaped similar to the tray 19 may be molded or otherwise provided on the housing lower side opposite the dispensing tray.

Larger diameter sized articles, such as the two different sized larger cross section diameter cylindrical shaped tampons 23 and 25, can also be dispensed to discharge opening 9. Depending on their diameters the roller's deformation will be greater for the greater cross section diameter tampon. Thus, the largest diameter tampon 25 will cause the greatest inward deformation of the roller's flexible body as it engages the roller and is dispensed through lower housing opening 9.

Figure 2:
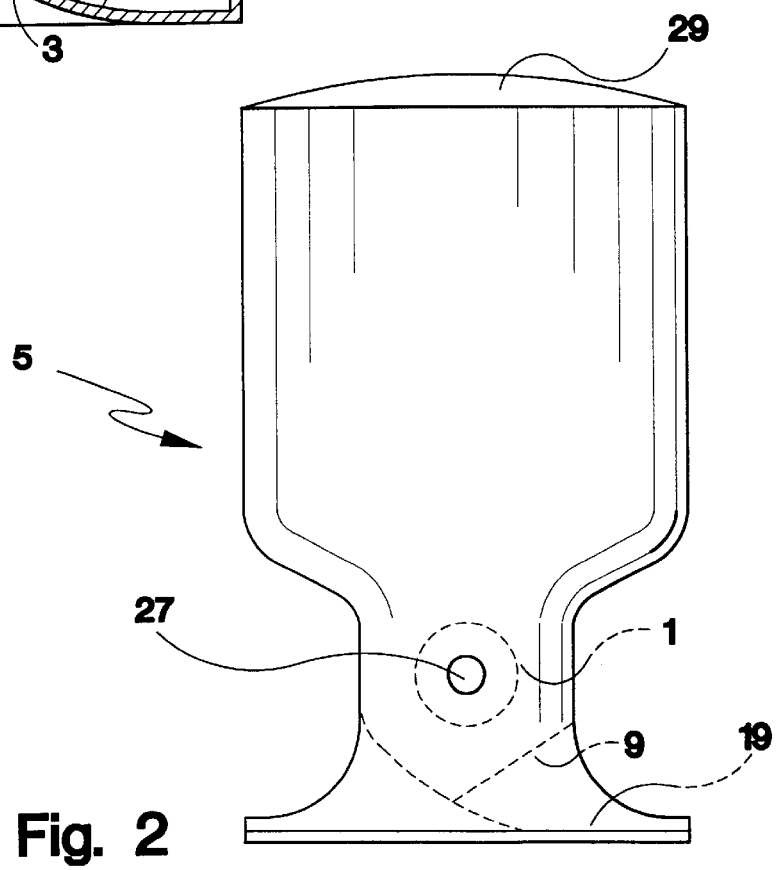
FIG. 2 is a side view of the FIG. 1 embodiment.

FIG. 2 is a side view of the FIG. 1 embodiment as viewed from the near side exterior wall surface of the housing 5. The flexible interior roller 1, located within the hollow housing, is shown in dotted line format. The roller's center straight shaft 3 is rotatably mounted at its two opposite ends into holes in the opposite side walls of the housing 5.

Two manually rotatable external knobs are fixed to the shaft's exposed external ends outside of the housing. One of these hand operated knobs 27 is shown the other being a duplicate thereof. By manually rotating either of the knobs in either direction, the roller 1 moves in unison with the knob in the same direction. Also shown in FIG. 2, is an upper snap fit removable lid 29 used to cover the housing opening 7 and permit the safe containment of articles within the housing until dispensed by rotating the roller 1. This top housing lid 29 has been removed from the FIG. 1 cross sectional housing view to simplify the drawings.

When used to dispense tampons of various diameter sizes the housing 5 can be made of a durable material with an attractive outer appearance. It may be made of a conveniently carried size that can easily fit within a handbag of a user. One example of the type of materials that could be used for the housing and its lid include plastic injected molded materials.

The deformable roller is rotatably mounted on its support shaft to the opposite sides of the housing with the two external control knobs mentioned. The roller can be made of any readily deformable material such as rubber, soft plastic foam material, or the like that can be deformed when the article to be dispensed is compressed against the roller and the housing's side wall at the adjacent location designated by the distance number 13.

The personal portable container and article dispenser provided for by this invention is not only simply to operate with one moving part, the roller assembly, it permits a user to have the advantages and convenience of an easily carried gravity fed portable tampon dispenser without the need to hunt for coins to operate a much more complex stand alone commercial dispensing machine.

In use the user removes the housing's upper lid 29 and inserts or fits the cylindrical tampons into the housing such that their lengths are aligned in a parallel manner with the length of the cylindrical roller 1 much like placing cigarettes in a cigarette case. To prevent clogging of the passageways when dispensed the tampons to be dispensed should have an overall length less than the length of the roller. When it is desired to dispense a single tampon seriatim, one of the two external housing knobs are rotated, in either direction, to engage the nearest tampon and move it under the influence of gravity to the discharge opening 9 and its holding tray 19. The user can then simply pick up the discharged tampon from the tray.

Although the present invention's preferred embodiment and the method of using the same according to the present invention has been described in the foregoing specification with considerable details, it is to be understood that modifications may be made to the invention which do not exceed the scope of the appended claims and modified forms of the present invention done by others skilled in the art to which the invention pertains will be considered infringements of this invention when those modified forms fall within the claimed scope of this invention.

What is claimed is:

1. An apparatus for dispensing articles one at a time from a container comprising:

a hollow container housing substantially closed on sides except for an upper article insert opening and a lower article dispensing opening;

an upper housing lid to engage the housing's article insert opening and retain articles within the container;

a flexible deformable article engaging roller rotatably mounted within the housing on the housing's sides near the housing's lower article dispensing opening, said roller being positioned within the housing to obstruct the movement of the contained articles against the force of gravity from being dispensed from the housing's dispensing opening;

articles within the container to be dispensed, said roller and the articles to be dispensed both being cylindrically shaped and oriented lengthwise parallel to each other, said dispensable articles have varying cross sectional diameters that can compress the deformable roller when positioned between the roller and the adjacent housing side walls, none said article diameters being greater than the lower housing opening; and means external to the housing including a manually operated knob mounted on the side of the housing, said knob being rotatable in unison with the roller to rotate the roller, said roller when in engagement with a stored article to be dispensed being deformed.

2. The apparatus as claimed in claim 1, wherein said roller is made of a deformable resilient material and is mounted on a center shaft whose two ends are attached to external control knobs.

* * * * *